United States Patent
Schmieding et al.

(10) Patent No.: US 7,591,820 B2
(45) Date of Patent: Sep. 22, 2009

(54) RETROGRADE OSTEOCHONDRAL AUTOGRAFT TRANSFER SYSTEM

(75) Inventors: Reinhold Schmieding, Naples, FL (US); Randall L. Hacker, Naples, FL (US); Timothy R. Hoover, Naples, FL (US)

(73) Assignee: Arthrex, Inc., Naples, FL (US)

( * ) Notice: Subject to any disclaimer, the term of this patent is extended or adjusted under 35 U.S.C. 154(b) by 677 days.

(21) Appl. No.: 10/637,536

(22) Filed: Aug. 11, 2003

(65) Prior Publication Data

US 2004/0034359 A1 Feb. 19, 2004

Related U.S. Application Data

(60) Provisional application No. 60/402,071, filed on Aug. 9, 2002.

(51) Int. Cl.
*A61B 17/00* (2006.01)
(52) U.S. Cl. ...................................................... 606/79
(58) Field of Classification Search .................. 606/79, 606/80, 86
See application file for complete search history.

(56) References Cited

U.S. PATENT DOCUMENTS

| | | | |
|---|---|---|---|
| 5,067,964 A * | 11/1991 | Richmond et al. ....... | 623/14.12 |
| 5,320,115 A * | 6/1994 | Kenna ...................... | 128/898 |
| 5,423,823 A * | 6/1995 | Schmieding ............... | 606/80 |
| 5,782,835 A * | 7/1998 | Hart et al. ................. | 606/79 |
| 5,833,628 A | 11/1998 | Yuan et al. | |
| 5,919,196 A | 7/1999 | Bobic et al. | |
| 6,007,496 A | 12/1999 | Brannon | |
| 6,358,253 B1 * | 3/2002 | Torrie et al. .............. | 606/96 |
| 6,375,658 B1 | 4/2002 | Hangody et al. | |
| 6,395,011 B1 * | 5/2002 | Johanson et al. ......... | 606/179 |
| 6,488,033 B1 * | 12/2002 | Cerundolo ................ | 128/898 |
| 6,592,251 B2 * | 7/2003 | Edwards et al. .......... | 366/268 |
| 6,852,114 B2 * | 2/2005 | Cerundolo ................ | 606/80 |
| 7,172,071 B2 * | 2/2007 | Hawkins ................... | 206/438 |
| 2004/0034437 A1 * | 2/2004 | Schmieding .............. | 623/908 |
| 2004/0210246 A1 * | 10/2004 | Johanson et al. ......... | 606/179 |

OTHER PUBLICATIONS

Lee et al., Operative Treatment of Osteochondritis Dissecans In Situ By Retrograde Driling and Cancellous Bone Graft: A Preliminary Report, 1981, Clinical Orthopedics and Related Research, Jul.-Aug., 129-136.*

* cited by examiner

*Primary Examiner*—Thomas C Barrett
*Assistant Examiner*—Nicholas Woodall
(74) *Attorney, Agent, or Firm*—Dickstein Shapiro LLP

(57) ABSTRACT

A retrograde osteochondral autograft transfer system that ensures that grafted healthy bone is implanted into the recipient site in a retrograde manner as opposed to a conventional anterior manner, so that the grafted healthy bone is flush with the bone surface of the recipient size. The retrograde osteochondral autograft transfer system of the present invention employs two identically-sized harvesters which are aligned with each other for transfer and reversal of a harvested osteochondral core, such that the core can be introduced into the recipient site through a tunnel leading to the recipient site, with an articular surface of the core advanced in a leading position.

12 Claims, 9 Drawing Sheets

US 7,591,820 B2

RETROGRADE OSTEOCHONDRAL AUTOGRAFT TRANSFER SYSTEM

This application claims the benefit of U.S. Provisional Application Ser. No. 60/402,071, filed Aug. 9, 2002, the entire disclosure of which is incorporated by reference herein.

FIELD OF THE INVENTION

The present invention relates to the field of surgery and, more particularly, to methods and apparatus for autogenous transplantation of articular cartilage/bone cores in knees.

BACKGROUND OF THE INVENTION

A method and apparatus for arthroscopic osteochondral autograft transplantation for repairing chondral defects is set forth in U.S. Pat. No. 5,919,196, the disclosure of which is incorporated by reference herein. The transplantation procedure of the '196 patent involves using matching graft harvesters and recipient site harvesters, in the form of tubes with collared pins, to create and to transplant donor graft osteochondral cores into corresponding sized recipient sockets.

Although the above-described procedure works well for defects on the femoral condyle, defects on the tibial plateau and the patella cannot be so easily accessed from the front side, as required in the technique of the '196 patent. Accordingly, it would be desirable to provide an apparatus and method for accessing the recipient site from the backside. Moreover, it is important that the contour of the donor plug, harvested from the femur, match the contour of the recipient site.

SUMMARY OF THE INVENTION

The present invention provides a retrograde osteochondral autograft transfer system that ensures that grafted healthy bone is implanted into the recipient site in a retrograde manner as opposed to a conventional anterior manner, so that the grafted healthy bone is flush with the bone surface of the recipient size. A first core harvester is employed to extract a healthy osteochondral core from a donor site. The harvested core is then reversed, in the preferred embodiment, by aligning the first core harvester with a similarly-sized second core harvester, so that the healthy osteochondral core is transferred from the first core harvester to the second core harvester. The healthy osteochondral core is inserted into the recipient site through a tunnel from the underside of the articular joint in a retrograde manner as opposed to a conventional anterior manner, so that the distal surface of the osteochondral core is flush to the articular surface of the recipient site.

Other features and advantages of the present invention will become apparent from the following description of the invention which refers to the accompanying drawings.

DETAILED DESCRIPTION OF THE INVENTION

The present invention provides a method for the osteochondral autograft transfer of a grafted core bone in a retrograde manner as opposed to a conventional anterior manner, so that the grafted core bone is implanted into a recipient damaged site and is flush with the bone surface of the recipient site. The retrograde osteochondral autograft transfer system of the present invention employs two harvesters which have the same size and which are aligned with each other for the retrograde delivery of the grafted core bone.

Figure 1:
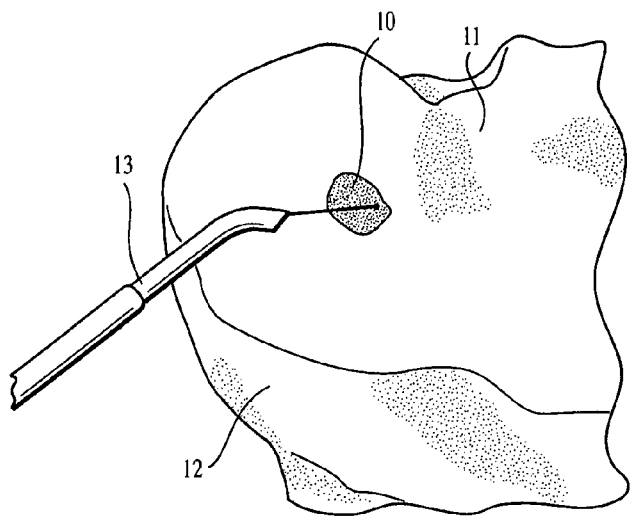
FIG. 1 illustrates an osteochondral lesion to be treated according to a method of the present invention.

Referring now to the drawings, where like elements are designated by like reference numerals, FIG. 1 depicts osteochondral lesion 10 located on tibial surface 11 of tibia 12. The osteochondral lesion 10 is a tibial plateau lesion of about 10 mm in diameter, as measured with measurement probe 13 (FIG. 1). As described below, the osteochondral lesion 10 is drilled out to create a recipient site for an angled harvested core 50 (FIGS. 15-16) grafted in accordance with a retrograde autograft method of the present invention.

Figure 2:
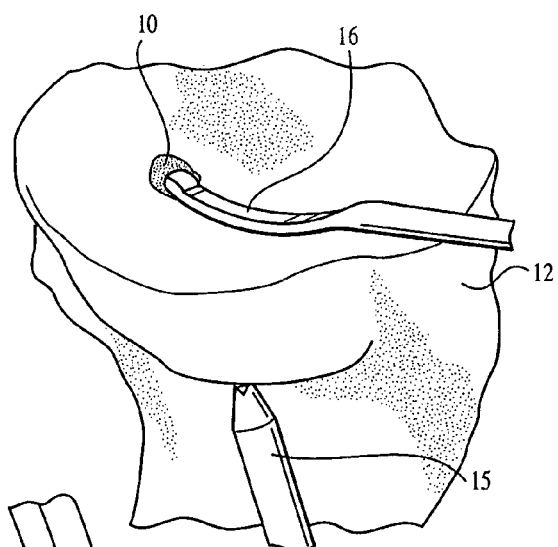
FIG. 2 illustrates the osteochondral lesion of FIG. 1 at a stage of treatment subsequent to that shown in FIG. 1.
Figure 3:
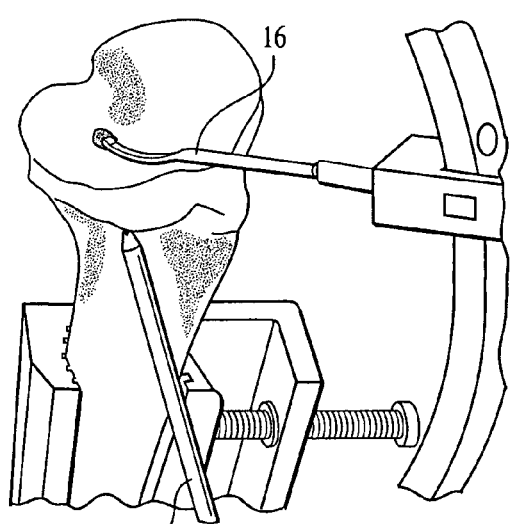
FIG. 3 illustrates the osteochondral lesion of FIG. 1 at a stage of treatment subsequent to that shown in FIG. 2.
Figure 4:
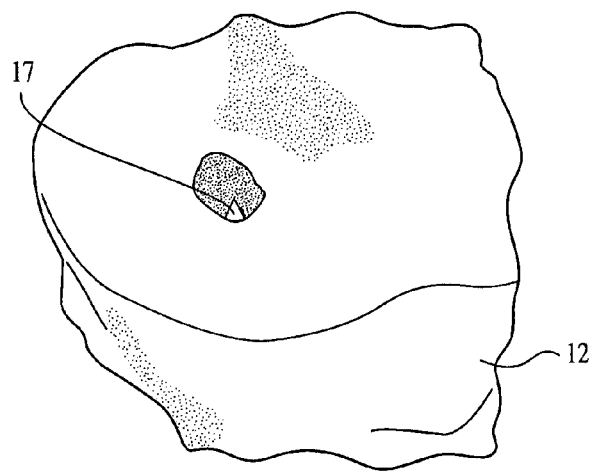
FIG. 4 illustrates the osteochondral lesion of FIG. 1 at a stage of treatment subsequent to that shown in FIG. 3.
Figure 5:
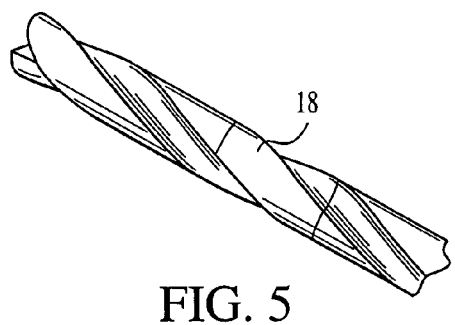
FIG. 5 illustrates a stepped drill for drilling through the osteochondral lesion of FIG. 1.
Figure 6:
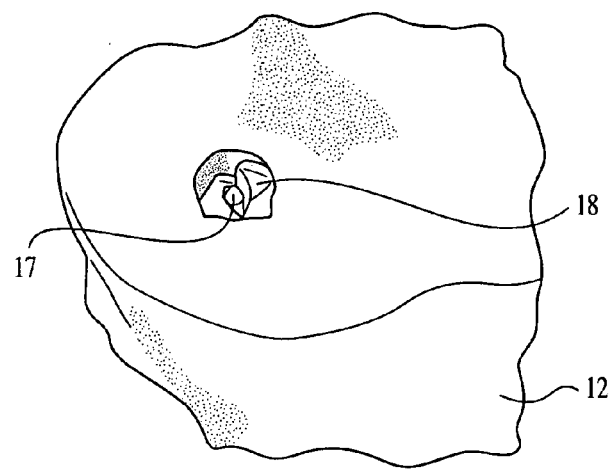
FIG. 6 illustrates the osteochondral lesion of FIG. 1 at a stage of treatment subsequent to that shown in FIG. 4.
Figure 7:
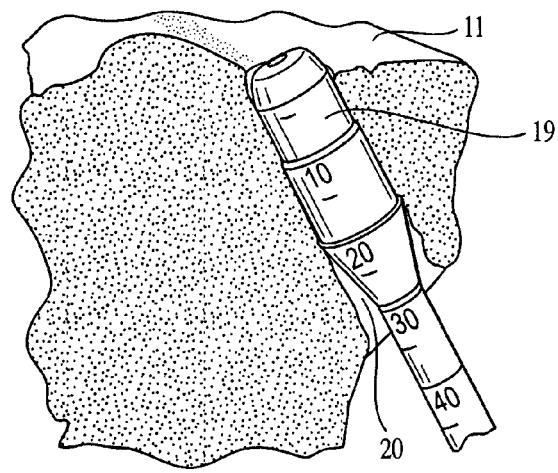
FIG. 7 illustrates a cross-sectional view of the osteochondral lesion of FIG. 1 at a stage of treatment subsequent to that shown in FIG. 6.
Figure 8:
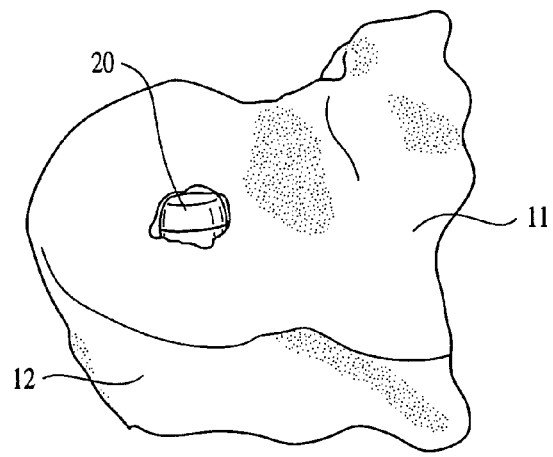
FIG. 8 illustrates the osteochondral lesion of FIG. 1 at a stage of treatment subsequent to that shown in FIG. 7.

An adapteur guide 15, such as Arthrex C-Ring Adapteur Guide, for example, is set at about 55° so that Arthrex OATS Marking Hook 16 is positioned in the center of the osteochondral lesion 10, as illustrated in FIGS. 2 and 3. In this manner, the Arthrex C-Ring Adapteur Guide 15 is positioned to drill guide pin 17 using a stepped drill 18, as illustrated in FIGS. 4-6. Stepped dialator 19 of about 10 mm is used to form a tunnel 20 through tibia 12 and to reach the tibial surface 11, as shown in FIGS. 7 and 8.

Figure 9:
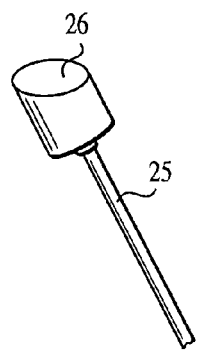
FIG. 9 illustrates a collared pin to be angled into the osteochondral lesion of FIG. 8.
Figure 10:
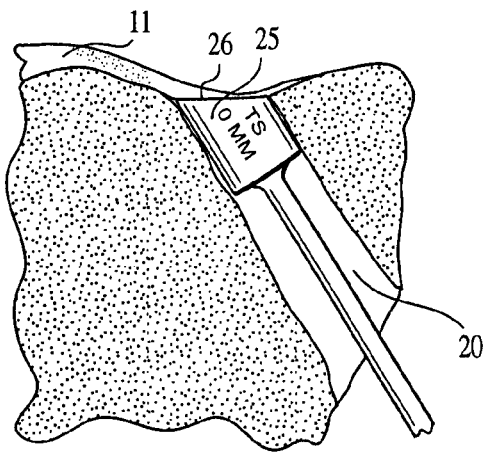
FIG. 10 illustrates a cross-sectional view of the osteochondral lesion of FIG. 1 at a stage of treatment subsequent to that shown in FIG. 8.
Figure 11:
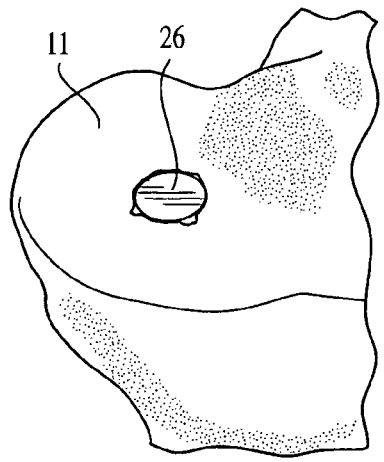
FIG. 11 illustrates the osteochondral lesion of FIG. 1 at a stage of treatment subsequent to that shown in FIG. 10.
Figure 12:
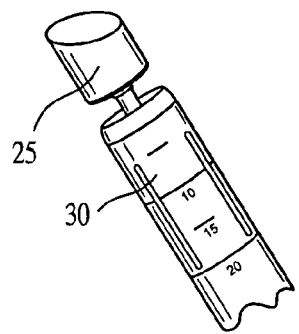
FIG. 12 illustrates an angled collared pin inserted into a donor harvester.

Collared pin 25 (FIG. 9) is next centered within the tunnel 20 (FIG. 10) and then properly angled at an angle "α" so that distal surface 26 of the collared pin 25 is flush with the tibial surface 11, as illustrated in FIG. 11. Properly angled collared pin 25 is subsequently inserted within a first donor harvester 30 (FIG. 12) to prepare for donor core harvesting. The first donor harvester 30 of FIG. 12 is similar to the graft harvester and recipient harvester of U.S. Pat. No. 5,919,196, the disclosure of which is incorporated by reference herein.

Figure 13:
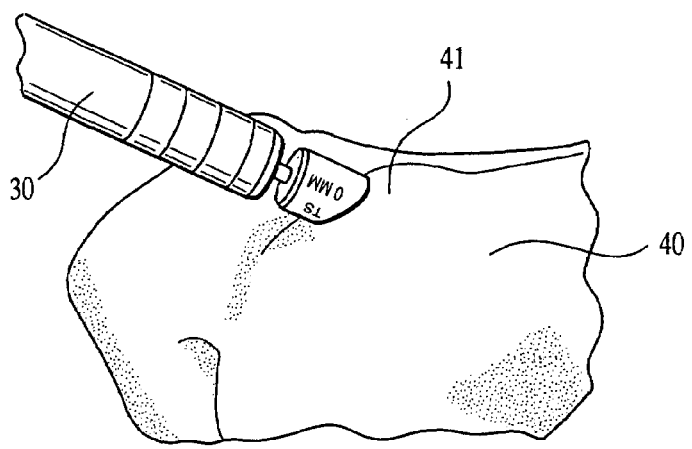
FIG. 13 illustrates the osteochondral lesion of FIG. 1 at a stage of treatment subsequent to that shown in FIG. 11.
Figure 14:
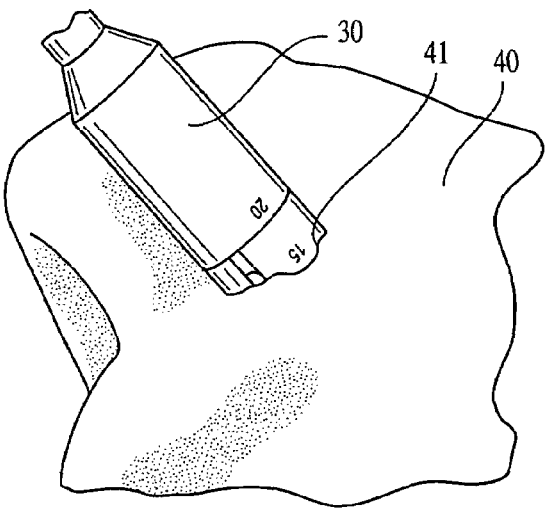
FIG. 14 illustrates the osteochondral lesion of FIG. 1 at a stage of treatment subsequent to that shown in FIG. 13.

Reference is now made to FIG. 13. The collared pin 25 is advanced out of the first donor harvester 30 to position the harvester 30 flat on the articular surface 41 of donor site 40. In this manner, the harvester 30 is impacted into the articular surface 41 of the donor site 40 following angle "α" established by the angled collared pin 25, as shown in FIGS. 13 and 14. The harvester 30 is driven into the bone of the donor site 40 by employing a mallet, for example. Care should be taken not to rotate the harvester 30 during insertion to avoid damaging the core to be harvested. Subsequent to the insertion into the bone of the donor site 40, the first donor harvester 30 is rotated, preferably about 90 degrees clockwise, about 90 degrees counter-clockwise, and then gently rocked, superior and inferior, to fracture the cancellous base for removal of angled harvested core 50 having a length L, which is about the length of the tibial tunnel 20 formed as described above. First donor harvester 30 is then retrograded from the donor site 40 with the harvested core 50 captured within the tube.

Subsequent to the extraction of the angled harvested core 50 from the donor site 40, the remaining donor socket is routinely left open after harvesting and filled in with cancerous bone and fibrocartilage within 8 to 12 weeks. Alternatively, cancellous bone harvested from the lesion 10 may be inserted into the donor site, and tamped firmly into the donor socket with a sizer/tamper or alignment stick to compress the cancellous bone for enhanced fixation.

Figure 15:
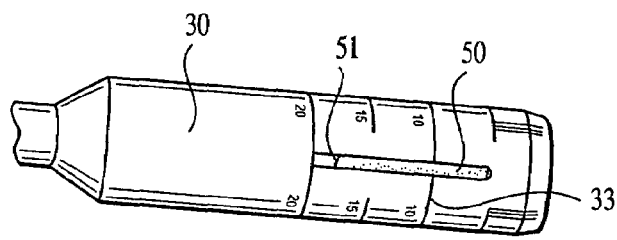
FIG. 15 illustrates the angled collared pin inserted into the donor harvester.
Figure 16:
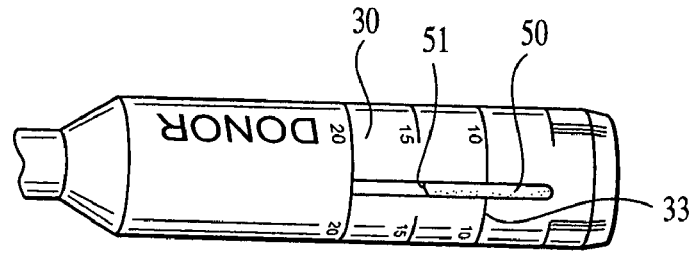
FIG. 16 illustrates another view of the angled collared pin inserted into the donor harvester of FIG. 15.

The angled harvested core 50 extracted from the donor site 40 can be visualized through windows 33 of the first donor harvester 30 to verify that the core has been captured successfully within the harvester. For example, FIGS. 15 and 16 illustrate two views of the harvester 30 with angled harvested core 50 at the highest point (FIG. 15) of its distal surface 51 and at the lowest point of its distal surface 51 (FIG. 16). If rotation and extraction of the tube harvester should fail to capture the core for removal, reinsertion and further impaction of the tube harvester up to 20 mm with subsequent rotation and extraction steps may be indicated.

Figure 17:
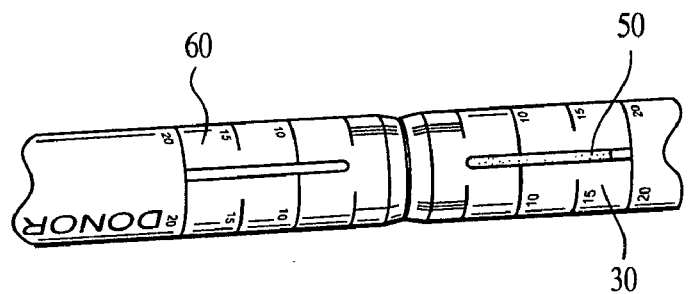
FIG. 17 illustrates the donor harvester of FIG. 16 aligned with another harvester.
Figure 18:
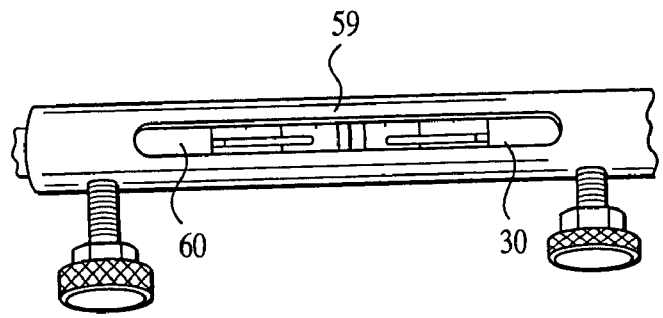
FIG. 18 illustrates the structure of FIG. 17 during stabilization.

Subsequent to the extraction of the angled harvested core 50 from the donor site 40, the first donor harvester 30 is brought into contact with and a second recipient harvester 60 for retrograde delivery. FIG. 17 illustrates the alignment of the first harvester 30 with the second harvester 60 to transfer the angled harvested core 50 of the first harvester 30 to the second harvester 60 for retrograde delivery. The second harvester 60 is of the same size as the first harvester 30. The tips of the first and second harvesters 50, 60 are subsequently stabilized in core exchange vice 59, and the angled harvested core 50 is transferred from the first harvester 30 to the second harvester 60, as shown in FIG. 18.

Figure 19:
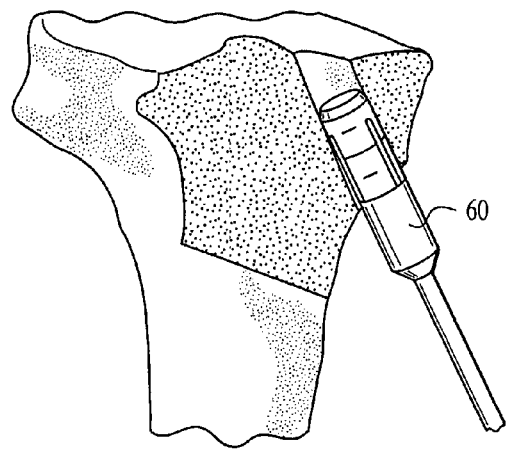
FIG. 19 illustrates a cross-sectional view of the osteochondral lesion of FIG. 1 at a stage of treatment subsequent to that shown in FIG. 14.
Figure 20:
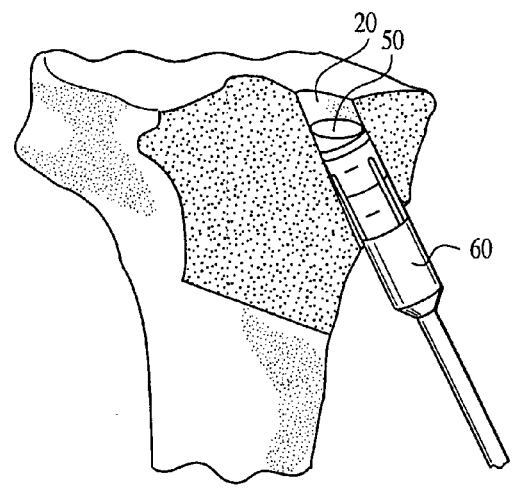
FIG. 20 illustrates a cross-sectional view of the osteochondral lesion of FIG. 1 at a stage of treatment subsequent to that shown in FIG. 19.
Figure 21:
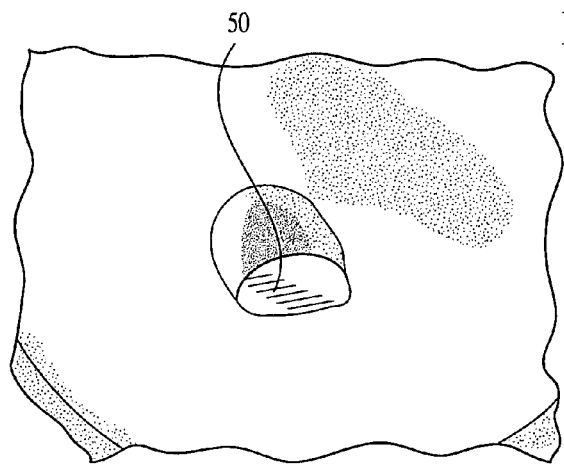
FIG. 21 illustrates the osteochondral lesion of FIG. 1 at a stage of treatment subsequent to that shown in FIG. 20.
Figure 22:
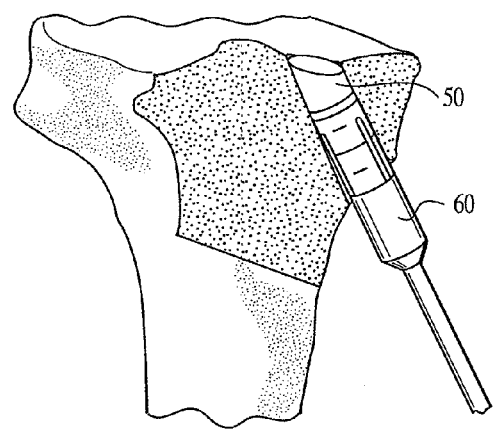
FIG. 22 illustrates a cross-sectional view of the osteochondral lesion of FIG. 1 at a stage of treatment subsequent to that shown in FIG. 21.
Figure 23:
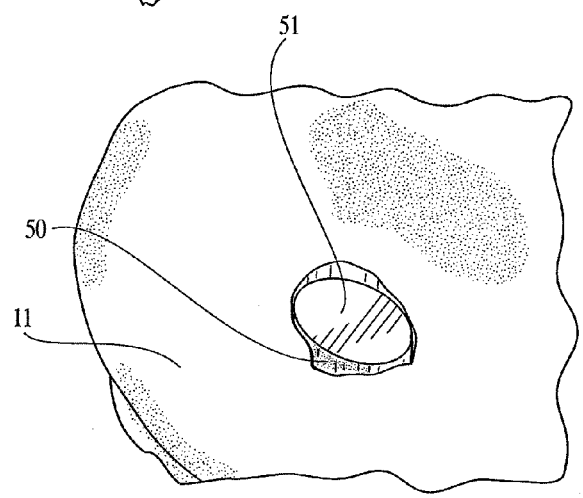
FIG. 23 illustrates the osteochondral lesion of FIG. 1 at a stage of treatment subsequent to that shown in FIG. 22.
Figure 24:
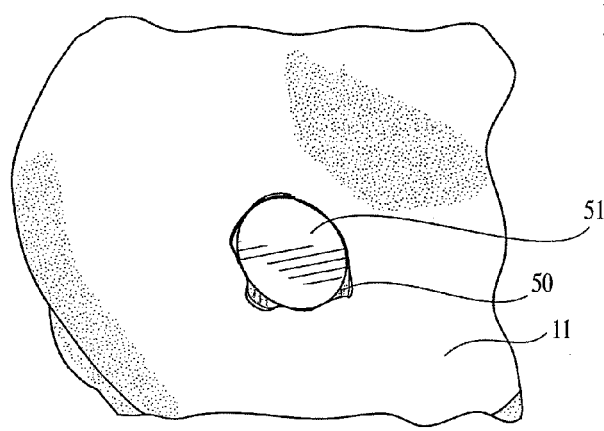
FIG. 24 illustrates the osteochondral lesion of FIG. 1 at a stage of treatment subsequent to that shown in FIG. 23.
Figure 25:
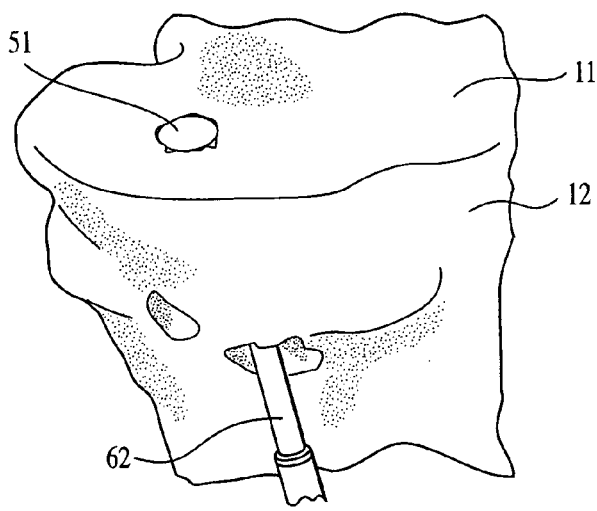
FIG. 25 illustrates the osteochondral lesion of FIG. 1 at a stage of treatment subsequent to that shown in FIG. 24.

Referring now to FIG. 19, the second harvester 60 with the angled harvested core 50 is next positioned within the tibial tunnel 20. The angled harvested core 50 is then expressed from the second harvester 60 into the tibial tunnel 20, as shown in FIGS. 20-22. FIG. 23 illustrates an incorrectly rotated angled harvested core 50; the distal surface 51 of the harvested core 50 is not flush with the tibial surface 11 of the tibia 12. FIG. 24 illustrates a properly rotated angled harvested core 50; the distal surface 51 of the harvested core 50 is flush with the tibial surface 11 of the tibia 12. For a finial rotation of the angled harvested core 50 within the tibial tunnel 20, the angled harvested core 50 may be backed-up with a bio-cortical screw 62, as shown in FIGS. 25-26.

Figure 26:
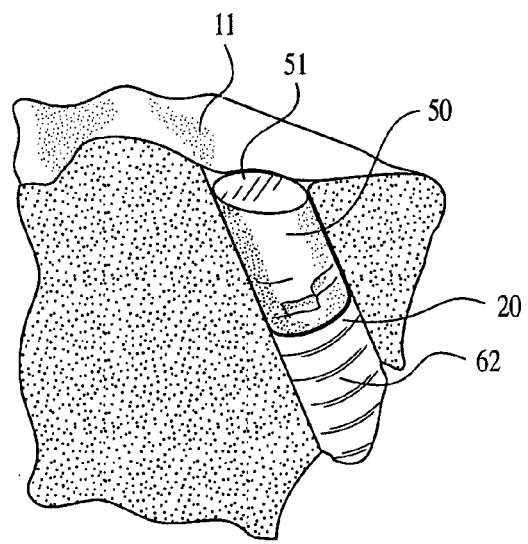
FIG. 26 illustrates a cross-sectional view of the osteochondral lesion of FIG. 1 at a stage of treatment subsequent to that shown in FIG. 25.
Figure 27:
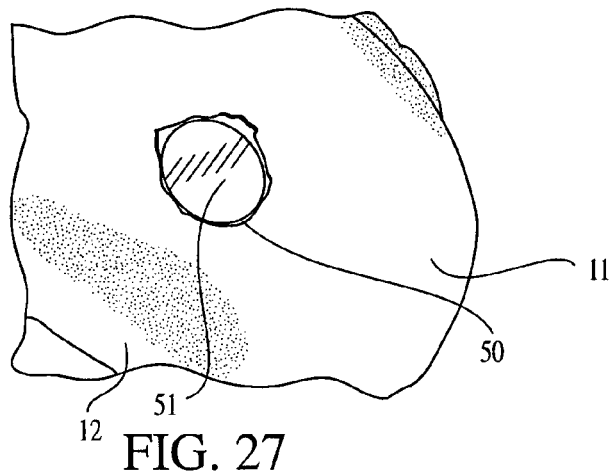
FIG. 27 is a top view of the structure of FIG. 25.

FIG. 26 illustrates a cross-sectional view of the tibial tunnel 20 of the tibia 12 with a three-dimensional view of the angled harvested core 50 implanted within the recipient or lesion site 10 in accordance with the retrograde osteochondral autograft transfer system of the present invention. FIG. 27 illustrates a top view of the angled harvested core 50 of FIG. 26, having distal surface 51 flushed with the surface 11 of the tibia 12.

Although the present invention has been described above with reference to a retrograde osteochondral autograft transfer system of the present invention illustrated in connection with a tibial lesion, it must be understood that this embodiment is only exemplary. Accordingly, the retrograde osteochondral autograft transfer system of the present invention has applicability to any damaged osteochondral area that requires replacement of osteochondral defects and core grafting. Also, although the present invention has been described above with reference to the retrograde delivery of an osteochondral core by employing two identically-sized harvesters, it must be understood that this embodiment is only illustrative and the invention is not limited to it. Accordingly, the invention also contemplates the retrograde delivery of an osteochondral core provided by using only one harvester, for example, and flipping the osteochondral core (by hand, for example), so that the flipped osteochondral core is subsequently inserted into the bone tunnel through the underside of the articular joint.

Additionally, although the present invention has been described above with reference to a retrograde osteochondral autograft transfer system for retrograde delivery of only one core having a predefined diameter and length, the invention also contemplates the retrograde delivery of multiple autograft cores of various diameters and various lengths, which are to be harvested and transferred into specific quadrants of the defect. If retrograde delivery of multiple autograft cores is desired, then preferably each core transfer should be completed prior to proceeding with further recipient socket creation. In this manner, potential recipient tunnel wall fracture are prevented and subsequent cores may be placed directly adjacent to previously inserted cores when desired.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

The invention claimed is:

1. A method of retrograde delivery of an osteochondral core into a recipient site, the method comprising the steps of:

forming a tunnel through bone leading to an articular surface of the bone at a recipient site corresponding an osteochondral defect;

harvesting an osteochondral core from a donor site with a first core harverster in an antegrade manner;

placing the first core harvester in a face-to-face configuration with a second core harvester, and transferring the harvested osteochondral core from the first core harvester to the second core harvester to reverse the orientation of the osteochondral core relative to its longitudinal axis, to obtain a reversed osteochondral core; and accessing the recipient site from its backside and from a location away from the articular surface of the bone, and inserting the reversed osteochondral core into the recipient site in a retrograde manner by inserting the reversed osteochondral core into the tunnel through an opening distal to the articular surface of the bone, such that an end of the reversed core is pushed up flush to the articular surface of the bone at the recipient site.

2. The method of claim 1, further comprising a step of measuring the contour of the articular surface of the recipient site by selecting a collared pin having a sloped distal surface corresponding to the slope of the articular surface at the recipient site.

3. The method of claim 2, wherein the step of measuring the contour of the articular surface of the recipient site is performed by inserting the collared pin into the tunnel so that the sloped distal surface of the collared pin is flush with the articular surface of the recipient site, to determine if the slope of the distal surface of the collared pin corresponds to the slope of the articular surface of the recipient site.

4. The method of claim 3, further comprising the steps of:
inserting the selected collared pin into the first core harvester;
positioning the first core harvester on a surface of a donor site;
advancing the collared pin through the first core harvester so that the distal surface of the collared pin is disposed against the articular surface of the donor site, such that the pin is disposed at an angle to the surface of a donor site; and
harvesting the osteochondral core by advancing the first core harvester into bone at the donor site with the collared pin disposed flush against the surface of the donor site, and harvesting the core while maintaining the angle of the pin.

5. A method of repairing an osteochondral defect in a bone, the method comprising the steps of:
forming a tunnel through the bone at a location corresponding to the location of the osteochondral defect in the bone;
harvesting in an antegrade manner, with a first core harvester, an osteochondral donor core from a donor site different from the location of the osteochondral defect in the bone;
transferring the harvested osteochondral donor core from the first core harvester to a second core harvester and simultaneously reversing the orientation of the osteochondral donor core to obtain a reversed osteochondral donor core; and
subsequently inserting the harvested osteochondral donor core in its reversed orientation into the bone tunnel through an opening of the tunnel distal to location of the osteochondral defect, the opening being at a location away from an articular surface of the bone and on a backside of the articular surface, and advancing the donor core such that an articular surface of the core is flush with the articular surface of the bone.

6. The method of claim 5, further comprising the step of selecting a collared pin with a distal surface that approximates the profile of the bone at the location of the osteochondral defect by inserting a collared pin into the bone tunnel having a distal surface which lies flush with the articular surface of the bone at the location of the osteochondral defect.

7. The method of claim 6, further comprising the steps of:
inserting the selected collared pin into the first core harvester; and
positioning the first core harvester with the selected collared pin at a donor site;
advancing the collared pin with the collared pin disposed flush against the surface of the donor site, such that the collared pin is disposed at an angle; and
driving the distal end of the first core harvester into the donor site to a predetermined depth to form the osteochondral core, while maintaining the angle of the collared pin.

8. The method of claim 5, wherein the step of inserting the harvested osteochondral donor core into the bone tunnel comprises inserting the core from the second core harvester into the bone tunnel through an opening of the tunnel opposite the osteochondral defect.

9. The method of claim 8, further comprising the step of removing the second core harvester from the tunnel subsequent to the step of inserting the osteochondral core.

10. The method of claim 5, wherein the first core harvester is similar in size to the second core harvester.

11. The method of claim 5, wherein the osteochondral core has a cancellous base.

12. A method of delivering an osteochondral core to a recipient site in a retrograde manner, the method comprising the steps of:
selecting a collared pin having an angled distal surface corresponding to the contour of the surface of a recipient site;
inserting the selected collared pin into a first core harvester;
impacting the first core harvester into a donor site in an antegrade manner to drive the first core harvester into the donor site to a predetermined depth to form an osteochondral core having an angled distal surface corresponding to the angled distal surface of the collared pin and the contour of the surface of the recipient site;
placing the first core harvester and a second core harvester in a face-to-face configuration and transferring the osteochondral core from the first core harvester into the second core harvester and simultaneously reversing the longitudinal orientation of the osteochondral core to obtain a reversed osteochondral core; and
accessing the recipient site from its backside and inserting the reversed osteochondral core into the recipient site which has a different location from that of the donor site, so that the angled distal surface of the osteochondral core is flush with the surface of the recipient site,
wherein the step of inserting the reversed osteochondral core into the recipient site comprises introducing the reversed osteochondral core into the recipient site through a tunnel leading to the recipient site, with the angled distal surface of the core in a leading position.

* * * * *

UNITED STATES PATENT AND TRADEMARK OFFICE
CERTIFICATE OF CORRECTION

PATENT NO. : 7,591,820 B2 Page 1 of 1
APPLICATION NO. : 10/637536
DATED : September 22, 2009
INVENTOR(S) : Schmieding et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1316 days.

Signed and Sealed this

Twenty-first Day of September, 2010

David J. Kappos
*Director of the United States Patent and Trademark Office*